Figure 1:
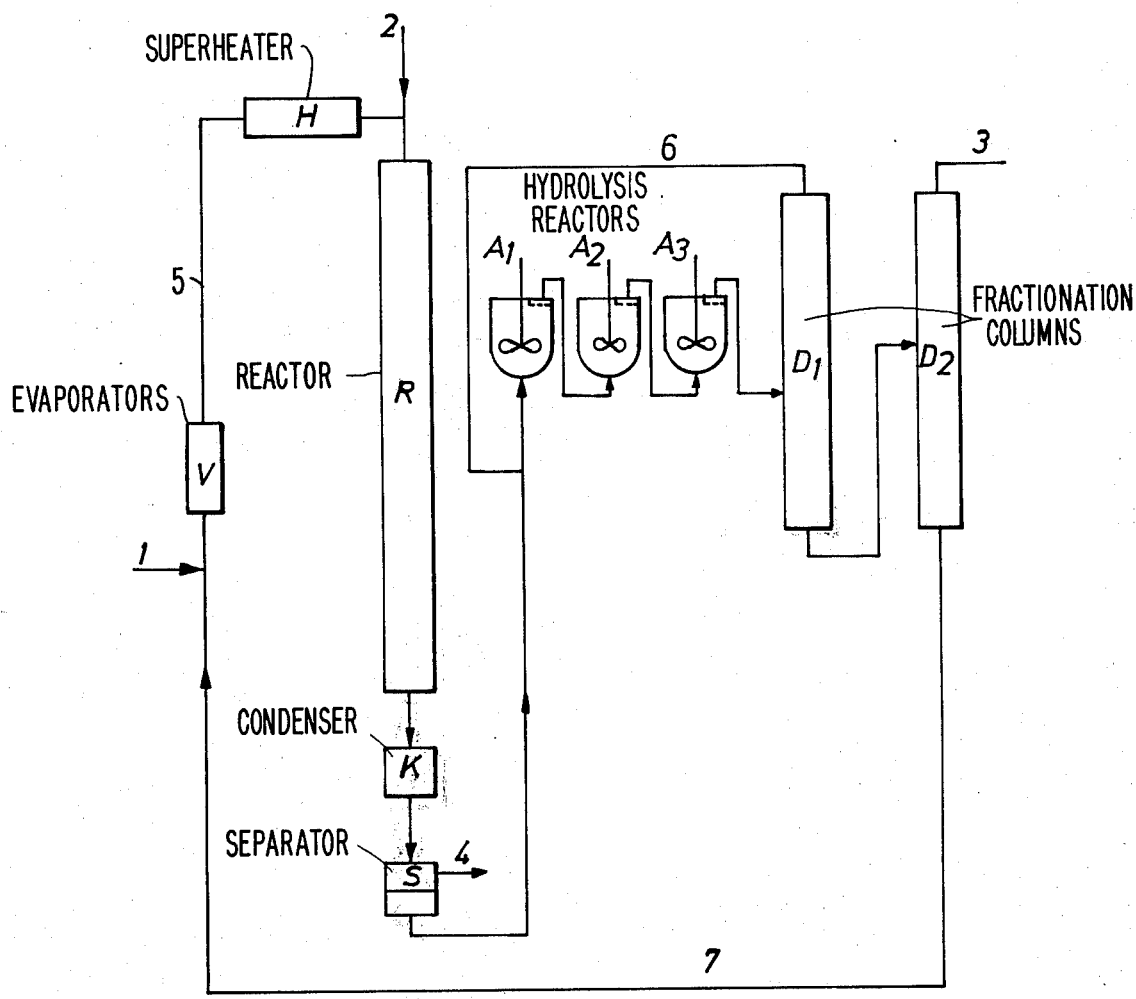

United States Patent [19]
Scharfe et al.

[11] 3,970,713
[45] July 20, 1976

[54] PROCESS FOR THE PRODUCTION OF ALLYL ALCOHOL

[75] Inventors: Gerhard Scharfe, Leverkusen; Wulf Schwerdtel, Cologne; Wolfgang Swodenk, Odenthal-Globusch; Bruno Engelhard, Cologne; Johann Grolig, Leverkusen; Manfred Martin, Cologne; Karl-Hermann Reissinger, Leverkusen, all of Germany

[73] Assignee: Bayer Aktiengesellschaft, Leverkusen, Germany

[22] Filed: Mar. 8, 1974

[21] Appl. No.: 449,418

Related U.S. Application Data

[63] Continuation of Ser. No. 50,341, June 26, 1970, abandoned.

[30] Foreign Application Priority Data

July 2, 1969 Germany............................ 1933538
Mar. 3, 1970 Germany............................ 2009742

[52] U.S. Cl.......................... 260/638 R; 260/497 A; 203/71; 203/84
[51] Int. Cl.$^2$......................................... C07C 29/00
[58] Field of Search.................. 260/638 R; 497 A; 203/71, 84

[56] References Cited
UNITED STATES PATENTS

| | | | |
|---|---|---|---|
| 2,428,590 | 10/1947 | Shokal et al. | 260/497 A |
| 2,441,540 | 5/1948 | Ash et al. | 260/638 R X |
| 2,485,694 | 10/1949 | Burchfield | 260/638 R |
| 2,650,249 | 8/1953 | Mention et al. | 260/541 |
| 2,936,321 | 5/1960 | Mercier | 260/638 R X |
| 3,190,912 | 6/1965 | Robinson | 260/497 A |
| 3,238,247 | 3/1966 | McKeon et al. | 260/497 A |
| 3,546,278 | 12/1970 | Hayden et al. | 260/497 A |
| 3,567,767 | 3/1971 | Yasui et al. | 260/497 A |
| 3,586,716 | 6/1971 | Yasui et al. | 260/638 R |
| 3,592,840 | 7/1971 | Durston et al. | 260/497 A |

FOREIGN PATENTS OR APPLICATIONS

| | | | |
|---|---|---|---|
| 1,387,791 | 12/1964 | France | 260/638 A |
| 1,101,055 | 1/1968 | United Kingdom | 260/497 A |

*Primary Examiner*—Howard T. Mars
*Attorney, Agent, or Firm*—Burgess, Dinklage & Sprung

[57] ABSTRACT

Allyl alcohol is produced in simple and economical fashion from propylene and oxygen by reacting propylene, oxygen and acetic acid over a palladium-containing catalyst in the presence of water; condensing the reaction product to form a condensate containing allyl acetate, acetic acid and water; treating the condensate with an acid catalyst and separating the resulting product by distillation into a head product consisting essentially of an allyl acetate/allyl alcohol/water azeotrope and into a sump product consisting essentially of acetic acid, allyl alcohol and water; recycling the head product to the acid catalyst stage; separating the sump product in a second distillation into an allyl alcohol/water head product and into a second sump product consisting essentially of acetic acid and water and recycling this sump product to the initial reaction.

18 Claims, 2 Drawing Figures

PROCESS FOR THE PRODUCTION OF ALLYL ALCOHOL

This is a continuation of application Ser. No. 50,341 filed June 26, 1970, now abandoned.

This invention relates to an economical process for the production of allyl alcohol by reacting propylene and oxygen.

It is known that allyl alcohol can be obtained by hydrolyzing allyl chloride or by isomerizing propylene oxide.

It has now been found that allyl alcohol can be obtained in commercially advantageous fashion from propylene and oxygen utilizing the process of this invention.

Essentially, the process comprises reacting propylene, oxygen and acetic acid in the gaseous phase over a palladium-containing catalyst in the presence of water at temperatures of from 50° to 250°C; condensing the gaseous reaction product to form a condensate comprising allyl acetate, acetic acid and water; treating said condensate with an acid catalyst in the liquid phase at temperatures of from 50° to 150°C in an acid catalyst treatment stage; and, after removal of the catalyst, separating the reaction product obtained in a first distillation column into a first head product consisting essentially of a ternary azeotrope of allyl acetate, allyl alcohol and water, and into a first sump product consisting essentially of acetic acid, allyl alcohol and water; recycling at least part of the first head product from said first distillation column to the said acid catalyst treatment stage; separating the first sump product from said first distillation column in a second distillation column into a second head product consisting essentially of the azeotrope of allyl alcohol and water and into a second sump product consisting essentially of acetic acid and water. The second sump product from the second distillation, is recycled to the reaction of propylene with oxygen and acetic acid, and the water in the azeotrope of allyl alcohol and water can be removed by methods known per se.

The process according to the invention begins with a reaction of propylene with oxygen and acetic acid to form allyl acetate. The gaseous reaction product can be condensed, for example, by cooling to a temperature below 50°C, resulting in the formation of a liquid phase which is separated from the remaining gaseous phase. The liquid phase consists essentially of allyl acetate, acetic acid and water. Depending upon the concentrations involved, the liquid phase may be separated into an upper organic phase consisting essentially of allyl acetate, and a lower aqueous phase consisting essentially of water and acetic acid. As already mentioned, the upper organic phase and the lower aqueous phase can be treated at least in part in the liquid phase with an acid catalyst. This can be carried out either at normal pressure or at elevated pressure, for example at pressures of from 2 to 5 atoms. The pressures are selected so that they are above the vapor pressure of the reaction mixture, ensuring that the reaction takes place in the liquid phase. Treatment with the acid catalyst is accompanied by partial hydrolysis of the allyl acetate into allyl alcohol. The catalyst is then removed from the reaction product either by neutralization, for example when sulfuric acid is used as the catalyst, or by mechanical separation, for example when an acid cation exchanger is used as the catalyst. The catalyst-free reaction product is separated in a distillation column into a head product consisting of a ternary azeotrope, boiling at approximately 83°C, of allyl acetate, allyl alcohol, water and acetic acid. The head product from this first column is recycled to the reaction with the acid catalyst. The sump product from the first column is divided up in a second distillation column into a head product consisting of the allyl alcohol-water azeotrope, and a sump product consisting of water and acetic acid which is recycled to the initial reaction of propylene, oxygen and acetic acid in the presence of water to form allyl acetate, thus completing the acetic acid circuit. Accordingly, propylene and oxygen only are required as starting materials for the reaction. The reaction can be illustrated by the following equation:

2 $C_3H_6$ + $O_2$ → 2 $C_3H_5OH$ (allyl alcohol)

Small quantities of carbon dioxide and water of reaction are formed as secondary products in the reaction of propylene with oxygen and acetic acid. This quantity of water, coupled with the formation of carbon dioxide, would increase the water content of the circuit in the case of complete recycling. In general, however, the quantity of water removed from the circuit, in the form of the allyl alcohol-water azeotrope, is greater than this water of reaction. Accordingly, it is usually necessary to supply a small quantity of water to the circuit in order to ensure a constant water content therein. In the process described in the foregoing, the allyl alcohol is obtained in the form of the water azeotrope boiling at 89°C and containing approximately 28% by weight of water. In many cases, the allyl alcohol may be directly used in the form of this water azeotrope for further chemical processing. Alternatively, the allyl alcohol may be freed from the water by conventional methods and thus obtained in the anhydrous form.

If the aforementioned main reaction by which allyl alcohol is formed in accordance with the equation:

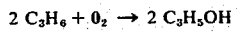
2 $C_3H_6$ + $O_2$ → 2 $C_3H_5OH$ is combined with the secondary reaction of formation of carbon dioxide through the combustion of propylene in accordance with the equation:

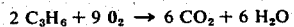
2 $C_3H_6$ + 9 $O_2$ → 6 $CO_2$ + 6 $H_2O$ it can be seen that allyl alcohol, carbon dioxide and water are formed in an overall reaction from propylene and oxygen, the water formed being the water of reaction formed during combustion of the propylene into carbon dioxide. Therefore, two substances, namely propylene and oxygen, have to be supplied to the reaction system as a whole. Three reaction components, namely allyl alcohol, carbon dioxide and water, have to be removed from the reaction system as a whole. Carbon dioxide is separated in the conventional manner from the recycled gas or from a component stream thereof, and removed in substantially pure form from the reaction system as a waste gas. If allyl alcohol were to be isolated in the anhydrous form during the process, the water of reaction accumulating during the formation of carbon dioxide would have to be removed from the liquid circuit, for example in the form of an aqueous acetic acid of the kind accumulating in the sump of the second distillation column. However, removal of the effluent containing acetic acid would involve a loss of acetic acid which, in general, is not economically acceptable, since special measures would have to be taken to recover the acetic acid from this effluent containing acetic acid. In the process according to the invention, the problem of processing an effluent containing acetic acid is solved by removing the water of reaction as a head product from the second distillation column in the form of the allyl alcohol-water azeotrope. In practice, therefore, two reaction products, namely carbon dioxide and the allyl alcohol-water azeotrope, are removed from the reaction system instead of three reaction products (allyl alcohol, water, carbon dioxide). In the practical application of the process, water is generally removed with the allyl alcohol-water azeotrope in a quantity greater than that formed through combustion of the propylene into carbon dioxide and water, and, therefore, the differential quantity is supplied to the system as a fresh quantity. It is of particular advantage to use this quantity of water for hydrolyzing the allyl acetate.

In a preferred embodiment of the process according to the invention, the following quantities are used for the reaction of propylene, oxygen and acetic acid into allyl acetate: 5 to 20 moles of water per mole of acetic acid, 1 to 5 moles of oxygen per mole of acetic acid and 4 to 40 moles of propylene plus inert constituents per mole of oxygen. The reaction temperature is adjusted to between 50° and 250°C. so that from 80 to 100% of the acetic acid used are reacted in a straight throughput. Cooling of the gaseous reaction product to a temperature below 50°C gives a liquid upper phase consisting essentially of allyl acetate, and a liquid lower phase consisting essentially of water.

The palladium present in the catalyst may be in the form of palladium metal or a compound thereof, which preferably is substantially free of halogens, sulfur and nitrogen; for example the palladium may be in the form of palladium acetate, palladium benzoate, palladium propionate, palladium acetylacetonate, or palladium hydroxide.

Metals or compounds affecting the activity and selectivity of the catalyst may also be added to the catalyst. Suitable additives of this kind include, for example, metals from the IV to VIII group of the Periodic System and/or gold and/or copper, which may also be in the form of compounds which are substantially free from halogen, sulphur and nitrogen. The following are mentioned as examples of additives: gold, platinum, iridium, ruthenium, rhodium in the form of metals, oxides or hydroxides, also oxides, hydroxides, acetates, acetylacetonates or decomposition and conversion products thereof of the elements iron, manganese, chromium, tungsten, molybdenum and vanadium. Preferred additives include iron compounds which are substantially free from halogen, sulfur and nitrogen, for example iron acetate, iron acetonylacetate, iron citrate, further manganese acetonylacetate, chromium acetonylacetonate, vanadiumacetylacetonate and sodiumvanadate. The catalysts are preferably applied to supports such as, for example, silica, natural and synthetic silicates, active carbon, aluminum oxide, spinels, pumice or titanium dioxide. It is preferred to use supports which have a high chemical resistance to water and acetic acid, such as silica, for example. The catalyst may be used, for example, in the form of pellets, micro-cylinders or spheres, for example in the form of spheres 4 to 6 mm in diameter.

The catalyst can be prepared in different ways. For example, compounds of the metals can be dissolved in a solvent, the support impregnated with the resulting solution and dried. It is also possible, however, successively to impregnate the support with the components which may then be optionally converted by an intermediate treatment, such as calcination or by chemical reactions, for example treatment with solutions of alkali metal hydroxides, alkali metal carbonates or reducing agents. The catalysts may be prepared from compounds containing sulfur, nitrogen or halogen, such as, for example, sodium palladium chloride, tetrachloroauric acid, iron chloride, copper nitrate or manganese sulphate, which are then converted on the support into insoluble compounds which are substantially free from sulfur, nitrogen and halogen, such as, for example, palladium metal, palladium oxide, iron hydroxide, gold hydroxide, copper hydroxide or manganese oxide, after which the catalyst is freed by washing from nitrogen, sulfur and halogen compounds.

For example, organic palladium and iron compounds may be applied together in an organic solvent and dried, for example, at a drying temperature of from 50° to 150°C, followed by the application of an alkali metal acetate from aqueous solution and then by drying at a temperature of from 50° to 200°C. Partial or complete decomposition or conversion of the organic palladium and iron compounds can take place under the drying conditions. The catalyst thus obtained can be treated with liquid or gaseous methanol, ethylene or propylene, to reduce the palladium compounds into palladium metal. It is also possible to treat the catalyst in the gaseous phase with propylene and water, optionally acetic acid and/or nitrogen and/or carbon dioxide before the reaction with propylene, acetic acid and oxygen to form allyl acetate, as a result of which the palladium compound can be reduced at least in part into the metal. The process according to the invention can be carried out either at normal pressure or at elevated pressure, preferably at pressures of from 3 to 15 atms.

In a preferred method of preparing the catalysts, palladium acetylacetonate and optionally iron acetylacetonate are dissolved in benzene, the catalyst support impregnated with the resulting solution, dried at 80° to 100°C, subsequently impregnated with potassium acetate from aqueous solution, the catalyst heated at 100° to 130°C and then treated in the gaseous phase with propylene and water and optionally acetic acid at a temperature of from 50° to 250°C, optionally under pressure. It is of commercial advantage to carry out this treatment in the reactor before the actual reaction into allyl acetate, i.e., before the oxygen is added. In another preferred method of preparing the catalysts, the support is impregnated with an aqueous sodium chloropalladate solution after which the sodium chloro palladate is treated with an aqueous sodium hydroxide solution to convert the palladium salt to a water/insoluble palladium hydroxide with is reduced into palladium metal with aqueous hydrazine. The catalyst is then washed with water, dried and then impregnated with potassium acetate.

The completed catalyst advantageously contains, expressed as the metal, from 1 to 10 g of Pd and from 1 to 100 g of alkali metal acetate per liter of the catalyst. In cases where other metals or metal compounds are used as additives, the completed catalyst may contain these metals, expressed as the metal, in quantities of, for example, from 0.1 to 10 g. The starting materials required for the production of allyl acetate should preferably be substantially free from halogen, sulfur and nitrogen compounds.

In addition to propylene, oxygen, acetic acid and water, the gas entering the reactor may contain inert constituents such as, for example, propane, carbon dioxide, nitrogen, argon. The concentration of oxygen at the inlet end of the reactor is advantageously selected so as to be below the explosion limit of the gaseous mixture present in the reactor.

The quantities of acetic acid and water are selected so that the reactants are in the gaseous phase under the reaction conditions.

In cases where small quantities of water are used, the alkali metal acetates gradually leave the catalyst. Although this is also the case in the procedure according to the invention, the volatility of the alkali metal acetate is significantly reduced by the presence of relatively large quantities of water. Accordingly, there is only a limited need for the alkali metal acetates to be continuously added. They may be added, for example, by introducing small quantities of alkali metal acetates, for example in the form of a dilute solution of the alkali metal acetate in water and/or acetic acid, into the hot gaseous stream before it enters the reactor. The solution may be directly sprayed in the liquid phase into the hot gas stream and volatilized there.

The reaction can be carried out in tubular reactors. Suitable dimensions of the reaction tubes include, for example, lengths of from 4 to 8 meters and internal diameters of, for example, from 20 to 50 mm. The heat of reaction can advantageously be dissipated by boiling cooling liquids which circulate around the outside of the reaction tubes, for example water under pressure. The reaction can also be carried out in a fluid bed. The reaction may be carried out, for example, by passing a recycle gas consisting essentially of propylene, oxygen and inert constituents such as carbon dioxide, propane, nitrogen and argon, under pressure through an evaporator containing acetic acid and water, and charging the recycled gas with the requisite quantity of acetic acid and water through the temperature prevailing in the evaporator.

The gaseous mixture is then heated under pressure to the reaction temperature and the oxygen required for the reaction introduced.

In order to counteract any formation and accumulation of relatively high boiling compounds in the sump of the acetic acid-water evaporator, small quantities of the sump product from the acetic acid-water evaporator can be run off either continuously or at intervals and optionally returned after purification, for examples by redistillation.

The gaseous phase accumulating during condensation following separation of the liquid components consists essentially of unreacted propylene, unreacted oxygen, carbon dioxide formed, and, optionally, inert constituents such as propane, nitrogen, argon. Depending upon the temperature and pressure at which the liquid components are separated, the gaseous phase contains certain quantities of the condensable reaction products such as water, allyl acetate and acetic acid. The gaseous phase can then be directly recycled under the reaction pressure as a recycle gas to the reaction and the acetic acid-water evaporator. It is also possible, however, to recover additional liquid components by varying the temperature and/or pressure, and to recycle the gas after these liquid components have been separated off.

The gas formed during the release of pressure from the liquid phase can be compressed and suitably recycled.

The carbon dioxide formed as a secondary product during the reaction of propylene to allyl acetate can be recycled into the reaction. In order to counteract an excessive accumulation of carbon dioxide, a component stream of the recycled gas can be removed from the circuit, thus maintaining a constant carbon dioxide content in the recycle gas, for example of from 20 to 30%, based on the recycled gas. The component stream can be returned to the recycled gas, following separation of the carbon dioxide.

The upper organic phase obtained, consisting essentially of allyl acetate, and the lower aqueous phase consisting essentially of water, are then combined at least in part and treated in the liquid phase with an acid catalyst. It is also possible to introduce the liquid condensate in the absence of phase separation into this treatment with the acid catalyst. Hydrolysis of the allyl acetate into allyl alcohol is carried out in the presence of an acid catalyst, for example a mineral acid or an acid cation exchanger. Liquid mineral acids such as sulfuric acid, for example, may be used for this purpose. In this case, the catalyst is removed and deactivated by neutralization, for example with sodium hydroxide, on completion of the reaction. Hydrolysis of the allyl acetate is advantageously carried out in the presence of an acid cation exchanger. Examples of suitable cation exchangers include sulfonated copolymers of styrene and divinylbenzene. The degree of crosslinking of the polystyrene sulfonic acids with divinylbenzene may amount to between 1 and 25% by weight, for example. On completion of the reaction, the catalyst is mechanically separated, for example by sedimentation, filtration or centrifuging, and the catalyst-free reaction product processed by distillation.

The allyl acetate may be hydrolyzed with advantage at a temperature in a range from 50° to 150°C. The reaction can be carried out either at normal pressure or even at elevated pressure, for example at pressures from 1 to 10 atms.

An equilibrium is attained during hydrolysis of the allyl acetate; the reaction product consists of allyl alcohol water, acetic acid and unreacted allyl acetate. The equilibrium can be displaced in favor of the allyl alcohol by increasing the water-allyl acetate ratio.

The reaction product freed from catalyst is separated in a first distillation column into a head product which boils at 82° to 84°C and consists of a ternary azeotrope of allyl acetate, allyl alcohol and water, and a sump product consisting of allyl alcohol, water and acetic acid. The ternary azeotrope removed overhead may have the following composition, as a typical example: allyl alcohol 9% by weight, water 20% by weight and allyl acetate 71% by weight. After condensation, it divides into two phases. The aqueous phase consists of 7% by weight of allyl alcohol, 89.9% of water and 3.1% by weight of allyl acetate, while the organic phase consists of 9.5% by weight of allyl alcohol, 5% by weight of water and 85.5% by weight of allyl acetate. A portion of the two phases may then either be delivered to the column as a reflux, or, preferably, a portion of the upper phase only can be delivered to the column as reflux and the lower phase completely used for hydrolysis.

The upper phase is recycled to the allyl acetate hydrolysis stage. The sump product from the first column is separated in a second column into an azeotrope consisting of allyl alcohol and water and boiling at 89°C and a sump product consisting of water and acetic acid. This sump product is recycled into the acetic acid-water evaporator where is is evaporated in the propylene-containing recycle gas stream, and then recycled to the reaction of propylene with oxygen and acetic acid.

Hydrolysis of the allyl acetate in a liquid phase with an acid cation exchanger may be carried out either continuously or at intervals. The continuous embodiment is preferred so far as commercial working of the process is concerned. To this end, a product containing allyl acetate and water can be continuously pumped into a pressure vessel equipped with a stirring mechanism, reacted with a suspended catalyst in the reaction vessel and a corresponding quantity of the reaction product removed continuously from the reaction vessel. In cases where a coarse-grained ion exchanger, for example in a grain size of from 0.5 to 1 mm, is used, separation of the catalyst from the reaction product can be obtained by removing it through a frit. It is also possible, however, to use a finely-ground ion exchanger and to separate the catalyst-containing reaction product in a centrifuge into a catalyst-free head product and a catalyst-containing sump product which is recycled to the reaction. In cases where a coarse-grained ion exchanger is used the catalyst can be introduced into a reaction tube through which the starting product flows. In this procedure, part of the reaction product can be recycled to the reaction and only a component stream removed from this circuit. It is also possible to arrange several reactors in series.

In a commercially advantageous embodiment of the hydrolysis of allyl acetate, acetic acid or allyl alcohol or mixtures of acetic acid and allyl alcohol are added as solution promotor to the condensation product to be treated with the acid catalyst. Allyl alcohol and acetic acid or mixtures of allyl alcohol and acetic acid are therefore suitable for use as solution promoters because they are formed during the hydrolysis of allyl acetate and hence do not represent foreign substances for carrying out the process. One possibility of adding these solution promoters is to recycle a partially hydrolysed mixture of allyl acetate and water, consisting of allyl acetate, water, allyl alcohol and acetic acid. However, the solution promoters can also be added in the form of allyl alcohol/water mixtures or acetic acid/water mixtures which accumulate during working up of the reaction product by distillation, for example during the first or second distillation. Experimental investigation into the influence of allyl alcohol and acetic acid as solution promoters for the allyl acetate/water system has shown that acetic acid has a better dissolving effect than allyl alcohol. Accordingly, the acetic acid may be added in concentrated form. Since acetic acid is only formed as an intermediate product in the process according to the invention for the production of allyl alcohol from propylene and oxygen and since hardly any fresh acetic acid is introduced into the system, it is of advantage to use acetic acid as solution promotor in the form in which it accumulates during the process. In one advantageous and preferred embodiment of the process, therefore, some of the recycle acetic acid which accumulates as sump product during the second distillation stage (allyl alcohol column) in the form of a mixture of from example 10 to 50% and preferably 25 to 35% of acetic acid in water, is recycled to the hydrolysis reaction. Aqueous acetic acid is added to the mixture of allyl acetate and water in at least such a quantity that the starting product for hydrolysis is homogeneously mixed under the working conditions applied, especially the operating temperature and the pressure. The homogeneous mixture consisting essentially of allyl acetate, water and acetic acid in addition to possibly small quantities of allyl alcohol, flows through a reactor filled with an acid catalyst, preferably an acid cation exchanger. The hydrolysis equilibrium is adjusted more or less completely in this reactor so that a mixture of allyl alcohol, water, allyl acetate and acetic acid, which can be split up, is removed at the end of this reactor, the ternary azeotrope of allyl acetate, allyl alcohol and water which can be recycled to hydrolysis, preferably being removed in the first distillation column. A mixture of allyl alcohol, water and acetic acid is then removed from the lower end of this column and in the second distillation column is separated into a head product consisting of an aqueous acetic acid containing for example approximately 30% of acetic acid. This aqueous acetic is partly recycled into the reaction of propylene with oxygen and acetic acid to form allyl acetate, another portion is recycled into the hydrolysis of the allyl acetate/water mixture in order to obtain at this point the homogeneous mixture of this system.

Figure 2:
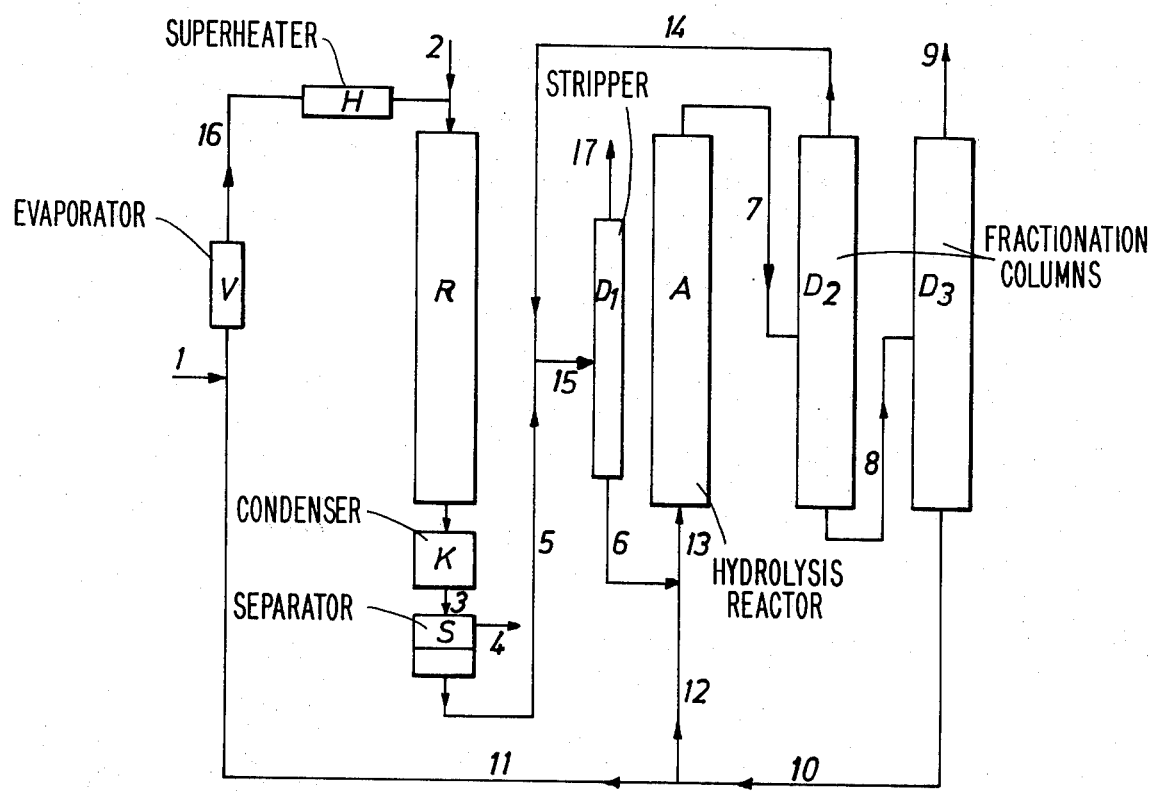

The production of allyl alcohol by reacting propylene and oxygen in accordance with the invention is illustrated in the following examples and drawings in which FIG. 1 is a flow-sheet of the process as it may be implemented in accordance with the invention, and FIG. 2 is a flow-sheet of an alternative embodiment of the process.

EXAMPLE 1

The test described in the following is illustrated in detail in FIG. 1 of the accompanying drawing.

The evaporator V contains the sump product from column D 2 consisting of acetic acid and water. Propylene introduced through feed line 1 was passed through the evaporator at a pressure of 5 atms. The temperature of the acetic acid-water mixture in the evaporator V was 120°C. In the evaporator V, the stream of propylene was charged with acetic acid and water corresponding to the vapor pressure. The mixture of propylene, water and acetic acid flowed through a pipe 5 to the superheater H in which it was heated to 170°C. Small samples of the gaseous mixture were taken behind the superheater H, and the molar ratio of water to acetic acid in the starting mixture of the reactor R determined. Oxygen was introduced through a pipe 2 in front of the reactor R. The reactor consisted of a jacketed pressure tube 2.50 meters long with an internal diameter of 25 mm cooled with boiling water under pressure. The reactor contained 1 liter of catalyst in the form of spheres 5 mm in diameter. The catalyst consisted of silica spheres with an inner surface of 120 $m^2/g$ containing 3.3 g of palladium in the form of palladium metal and 30 g of potassium acetate per liter of the catalyst. The reactor was kept at a temperature of 168°C. The gaseous reaction product was cooled to 20°C in a condenser K under a reaction pressure of 5 atms., followed in the following pressure vessel S by phase separation to a gaseous phase and a liquid phase. The gaseous phase was removed through a pipe 4. It consisted of unreacted propylene and unreacted oxygen. It also contained small quantities of carbon dioxide formed as a secondary product in the reactor. Following removal of the carbon dioxide formed during the reaction, the unreacted propylene and unreacted oxygen from stream 4 were recycled to the reaction through pipe 1. The liquid reaction product from the separation vessel S, consisting of allyl acetate, acetic acid and water, was pumped into three successive autoclaves A1, A2 and A3, each equipped with a stirring mechanism. Each of these autoclaves contained 100 g of acid cation exchanger (polystyrene sulfonic acid, crosslinked with 8% of divinylbenzene, H-form). The reaction of the liquid reaction product from the separation vessel S in the autoclaves A1, A2 and A3 was carried out in the liquid phase at a temperature of 100°C under a pressure of 3 atms. The reaction product was removed from the autoclaves free from catalyst through frits. The catalyst-free reaction product from autoclave A3 was separated in a distillation column D1 into a head product boiling at 83°C and a sump product. The head product was recycled through pipe 6 to autoclave A1. The sump product from column D1 was separated in the column D2 into a head product boiling at 89°C and a sump product. The head product consisted of the azeotrope of allyl alcohol and water. It was removed from the system through a pipe 3 as the required end product. The sump product from the column D2 was returned through a pipe 7 to the evaporator B.

A balance test was carried out for a period of 500 hours during which the ratio of water to acetic acid in the starting product was continuously checked by analyzing the starting product behind the superheater H. A ratio of (7 ± 2) moles of water per mole of acetic acid was adjusted by adding small quantities of water to the starting product of evaporator B. A total of 46.2 kg of propylene and 15.2 kg of oxygen was reacted in the 500 hour test. 58 kg of allyl alcohol, based on anhydrous alcohol, were obtained at the head of column 2. In accordance with the equation:

$$2\ C_3H_6 + O_2 \rightarrow 2\ C_3H_5OH \text{ (allyl alcohol)}$$

this corresponds to a yield of 90%, based on propylene, and to a yield of 52.6%, based on the oxygen used.

EXAMPLE 2

The procedure was as in Example 1, except that two reaction tubes were filled with an ion exchanger (polystyrene sulfonic acid, crosslinked with 8% of divinyl benzene, H-form) with a grain size of from 0.5 to 1.2 mm, were used instead of the autoclaves A1, A2 and A3. A mixture of the liquid reaction product from the separation vessel S, of head product from column D1 and recycled reaction product from the first reaction tube, flowed upwards through the first reaction tube at 105°C under a pressure of 3 atms. So much reaction product from the hydrolysis stage was recycled that the two phases are homogeneously mixed at room temperature. The reaction product was removed behind the first reaction tube corresponding to the quantity of product from separation vessel S and head product from D1 supplied, passed upwards through the second reaction tube at a pressure of 3 atms. and at a temperature of 100°C and was then introduced into the distillation column D1.

46.0 kg of propylene and 15.0 kg of oxygen was reacted in a 500 hour test. 58 kg of allyl alcohol was obtained, based on anhydrous allyl alcohol.

EXAMPLE 3

The procedure described in the following is illustrated in detail in FIG. 2.

The sump product from column D3 consisting of acetic acid and water was accommodated in the evaporator V. Propylene delivered through pipe 1 was passed through evaporator V at a pressure of 5 atmospheres. The temperature of the mixture of acetic acid and water in evaporator V was 120°C. In evaporator V, the stream of propylene was charged with water and acetic acid corresponding to the vapor pressure. The mixture of propylene, water and acetic acid flowed through pipe 16 to the superheater H in which it was heated to 170°C. Small samples of the gaseous mixture could have been taken behind the superheater H and the molar ratio of water to acetic acid in the starting mixture for reactor R determined. Oxygen was added before reactor R through the pipe 2. The reactor consisted of a pressure tube 2.50 meters long with an internal diameter of 25 mm which was cooled with boiling pressure water. One liter of catalyst in the form of 5 mm diameter spheres was accommodated in the tube. The catalyst consisted of silica spheres with an inner surface of 120 m²/g containing 3.3 g of palladium in the form of palladium metal and 50 g of potassium acetate per liter of catalyst. The reactor was kept at a temperature of 168°C. The gaseous reaction product was cooled to 20°C in the condenser K under the reaction pressure of 5 atmospheres. Separation into a gas phase and a liquid phase took place in the following separation vessel S. The gas phase was removed through pipe 4. It consisted of unreacted propylene and unreacted oxygen and of liquid reaction products corresponding to their vapor pressure. It also contained small quantities of carbon dioxide formed as secondary product in the reactor. Following removal of the carbon dioxide formed during the reaction in known manner by washing for example with hot carbonate solution, the unreacted propylene and the unreacted oxygen from stream 4 was recycled through pipe 1 into the reaction. The liquid reaction product from the separation vessel S consisting essentially of allyl acetate, water and small quantities of acetic acid, was delivered through pipes 5 and 15 to the stabilizing column D1, in which it was freed from dissolved gas (especially propylene) which gas was removed via line 17, and optionally from small quantities of low-boiling constituents (for example acrolein, propionaldehyde). The actual liquid reaction product consisting essentially of allyl acetate and water in addition to small quantities of acetic acid, was run off at the lower end of the column through pipe 6. This stream 6 was mixed with a stream 12 consisting essentially of water and acetic acid. So much product was delivered through pipe 12 that a homogeneous phase was formed at 80°C in admixture with the product from pipe 6. The homogeneous mixture of allyl acetate, water and acetic acid which contains small quantities of allyl alcohol through the addition of a recycle product through pipes 14 and 15 to column D1, was delivered through pipe 13 to a reaction tube 2.50 meters long with an internal diameter of 25 mm. This reaction tube was filled with one liter of an ion exchanger (polystyrene sulfonic acid crosslinked with 8% of divinylbenzene, H-form) with a grain size of from 0.5 to 1.2 mm. The product from pipe 13 flowed upwards through this reaction tube. Hydrolysis of the allyl acetate was carried out in the reactor at a temperature of 105°C and at a pressure of 2 atms. A reaction product consisting of allyl alcohol, allyl acetate, water and acetic acid was removed from the head of reactor A through pipe 7. This product was separated in column D2 into a head product boiling at 83°C and a sump product. The head product which consisted of the ternary azeotrope of allyl acetate, allyl alcohol and water was delivered to column D1 through the pipes 14 and 15. The sump product of column D2 which consisted of allyl alcohol, water and acetic acid, was delivered to column D3 through pipe 8. Allyl alcohol was run off from the head of column D3 in the form of its azeotrope of allyl alcohol and water boiling at 89°C. An aqueous acid was removed from the lower end of column D-3 and was recycled partly to reactor A through pipes 12 and 13 and partly to the acetic acid evaporator V through pipe 11.

EXAMPLE 4

A balance test of 500 hours duration was carried out as in Example 3. During this period, the ratio of water to acetic acid in the starting product was continuously checked by analyzing the starting product behind the superheated H, and a ratio of $7 \pm 2$ moles of water per mole of acetic acid was adjusted by adding small quantities of water to the starting product of the evaporator V. The water added at this point had been used as a washing agent for removing small quantities of acetic acid in the gas which was subjected to a $CO_2$-wash in order to avoid any losses of acetic acid. A total of 46 kg of propylene and 15 kg of oxygen was reacted during the 500-hour test. 58 kg of allyl alcohol, expressed as anhydrous allyl alcohol, were obtained at the head of column D3. According to the equation

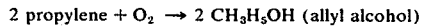

2 propylene + $O_2$ → 2 $CH_3H_5OH$ (allyl alcohol)

this corresponds to a yield of 90% based on propylene.

What is claimed is:
1. Process for the production of allyl alcohol which comprises
   a. reacting propylene, oxygen and acetic acid in the gaseous phase over a palladium-containing catalyst consisting essentially of palladium metal, an alkali metal acetate, and optionally a Group IV to VIII metal, copper or gold or a compound yielding such metal, said catalyst being free of halogen, sulfur and nitrogen, in the presence of 5 to 20 moles of water per mole of acetic acid at temperatures of from 50° to 250°C.;
   b. condensing the gaseous reaction product to form a condensate comprising allyl acetate, acetic acid and water;
   c. treating said condensate with an acid cation exchanger catalyst in the liquid phase at temperatures of from 50° to 150°C. in an acid catalyst treatment stage; and
   d. after removal of the catalyst, separating the reaction product obtained in a first distillation column into a first head product consisting essentially of a ternary azeotrope of allyl acetate, allyl alcohol and water, and into a first sump product consisting essentially of acetic acid, allyl alcohol and water;
   e. recycling at least part of the first head product from said first distillation column to the said acid catalyst treatment stage;
   f. separating the first sump product from said first distillation column in a second distillation column into a second head product, consisting essentially of the azeotrope of allyl alcohol and water, and into a second sump product consisting essentially of acetic acid and water;
   g. recycling the second sump product to the initial reaction of propylene with oxygen and acetic acid; and
   h. removing the allyl alcohol-water azeotrope.

2. A process as claimed in claim 1 wherein the palladium containing catalyst contains an alkali metal compound which is converted at least partly into said alkali metal acetate under the reaction conditions.

3. Process as claimed in claim 1 wherein the palladium-containing catalyst contains from 1 to 10 grams of Pd, in terms of contained metal, and from 1 to 100 grams of alkali metal acetate, per liter of the catalyst.

4. Process as claimed in claim 1 wherein the gaseous reaction product from the reaction of propylene, oxygen and acetic acid is cooled under pressure to a temperature below 50°C. and the liquid product formed is separated from the gaseous product.

5. Process as claimed in claim 1 wherein a ratio from 5 to 20 moles of water are provided per mole of acetic acid, for the reaction between propylene, oxygen and acetic acid, and the reaction temperature is from 50° to 250°C. to react from 80 to 100% of the acetic acid reactant in one throughput.

6. Process as claimed in claim 1 wherein the catalyst contains an iron compound.

7. Process as claimed in claim 1 wherein treatment of the reaction product from the reaction of propylene, oxygen and acetic acid with the acid catalyst is carried out continuously in several reactors arranged in sequence.

8. Process as claimed in claim 1 wherein fresh water is introduced into the allyl acetate hydrolysis stage in order to maintain the water content throughout the entire reaction system.

9. Process as claimed in claim 1 wherein the head product is condensed in a first distillation column, separated into an organic upper phase and an aqueous lower phase, part of the upper phase is delivered to the column as reflux and the lower aqueous phase is directly used for hydrolysis.

10. Process as claimed in claim 1 wherein acetic acid or allyl alcohol or mixtures of acetic and allyl alcohol are added as a solution promoter to the condensation product treated with the acid catalyst.

11. Process as claimed in claim 1, wherein the condensation product is treated with an acid cation exchanger and at the same time acetic acid or allyl alcohol or mixtures of acetic acid and allyl alcohol are added as a solution promoter in such a quantity that the condensation product to be treated is homogeneously mixed with the acid cation exchanger.

12. Process as claimed in claim 10, wherein some of the sump product from the second distillation is used as a solution promoter.

13. Process as claimed in claim 10, wherein a reaction product from acid catalyst treatment stage which, in addition to allyl acetate and water, contains allyl alcohol and acetic acid formed by hydrolysis of the allyl acetate, is used as a solution promoter.

14. Process as claimed in claim 1, wherein the condensation product, prior to hydrolysis, is freed in a distillation column from dissolved gases and/or compounds with a lower boiling point than the ternary azeotrope of allyl acetate, allyl alcohol and water.

15. Process as claimed in claim 1 wherein said acid catalyst is polystyrene sulfonic acid cross-linked with divinylbenzene.

16. Process as claimed in claim 1 wherein the acid catalyst treatment is conducted at super-atmospheric pressure of from 2 to 5 atmospheres.

17. Process as claimed in claim 2 wherein said alkali metal acetate is potassium acetate.

18. Process as claimed in claim 1 wherein said oxygen is supplied at a rate of from 1 to 5 mols of oxygen per mol of acetic acid, and said propylene is supplied at a rate of from 4 to 40 mols of propylene (plus inert constituents) per mol of oxygen.

* * * * *